US008530682B2

(12) United States Patent
Sachs et al.

(10) Patent No.: US 8,530,682 B2
(45) Date of Patent: Sep. 10, 2013

(54) PROCESS FOR EPOXIDATION START-UP

(75) Inventors: Howard Sachs, Bronx, NY (US);
Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 391 days.

(21) Appl. No.: 12/970,392

(22) Filed: Dec. 16, 2010

(65) Prior Publication Data
US 2011/0152548 A1 Jun. 23, 2011

Related U.S. Application Data

(60) Provisional application No. 61/287,393, filed on Dec. 17, 2009.

(51) Int. Cl.
*C07D 301/10* (2006.01)
(52) U.S. Cl.
USPC .......................................... 549/536; 549/534
(58) Field of Classification Search
USPC .................................. 549/534, 536
See application file for complete search history.

(56) References Cited

U.S. PATENT DOCUMENTS

| 3,563,914 | A | 2/1971 | Wattimena |
|---|---|---|---|
| 3,702,259 | A | 11/1972 | Nielsen |
| 4,761,394 | A | 8/1988 | Lauritzen |
| 4,766,105 | A | 8/1988 | Lauritzen |
| 4,874,879 | A | 10/1989 | Lauritzen et al. |
| 4,908,343 | A | 3/1990 | Bhasin |
| 5,011,807 | A | 4/1991 | Hayden et al. |
| 5,057,481 | A | 10/1991 | Bhasin |
| 5,099,041 | A | 3/1992 | Hayden et al. |
| 5,102,848 | A | 4/1992 | Soo et al. |
| 5,155,242 | A | 10/1992 | Shankar et al. |
| 5,187,140 | A | 2/1993 | Thorsteinson et al. |
| 5,407,888 | A | 4/1995 | Herzog et al. |
| 5,856,534 | A | 1/1999 | Cooker et al. |
| 7,102,022 | B2 | 9/2006 | Evans et al. |
| 7,553,980 | B2 | 6/2009 | Rizkalla et al. |
| 2004/0110971 | A1 | 6/2004 | Evans et al. |
| 2007/0032670 | A1 | 2/2007 | Zhang et al. |
| 2007/0037991 | A1 | 2/2007 | Rizkalla |
| 2011/0152073 | A1 | 6/2011 | Dialer et al. |

FOREIGN PATENT DOCUMENTS

EP       0352849 A1    1/1990

OTHER PUBLICATIONS

International Search Report dated Sep. 9, 2011 received in a corresponding foreign application.
Extended European Search Report dated Apr. 24, 2013 received in a corresponding foreign application.

*Primary Examiner* — Bernard Dentz
(74) *Attorney, Agent, or Firm* — Scully, Scott, Murphy & Presser, P.C.

(57) ABSTRACT

A method for the start-up of a process for the epoxidation of ethylene comprising: initiating an epoxidation reaction by reacting a feed gas composition containing ethylene, and oxygen, in the presence of an epoxidation catalyst at a temperature of about 180° C. to about 210° C.; adding to the feed gas composition about 0.05 ppm to about 2 ppm of moderator; increasing the first temperature to a second temperature of about 240° C. to about 250° C., over a time period of about 12 hours to about 60 hours; and maintaining the second temperature for a time period of about 50 hours to about 150 hours.

13 Claims, No Drawings

US 8,530,682 B2

PROCESS FOR EPOXIDATION START-UP

RELATED APPLICATION

This application claims benefit of U.S. Provisional Patent Application Ser. No. 61/287,393, filed Dec. 17, 2009, the entire content of which is incorporated herein by reference.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Thèodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 15 billion tons. (About two thirds of the ethylene oxide produced is further processed into ethylene glycol, while about ten percent of manufactured ethylene oxide is used directly in applications such as vapor sterilization.)

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is Ag-based epoxidation catalysts that contain small amounts of "promoting" elements such as rhenium and cesium.

With respect to these Re-containing catalysts, there has been considerable interest in determining the optimum start-up (also commonly referred to as "initiation" or "activation") conditions, since Re-containing catalysts require an initiation period to maximize selectivity.

Initiation procedures were previously disclosed in U.S. Pat. No. 4,874,879 to Lauritzen et al. and U.S. Pat. No. 5,155,242 to Shanker et al., which disclose start-up processes in which a Re-containing catalyst is pre-chlorinated prior to the introduction of oxygen into the feed and the catalyst is allowed to "pre-soak" in the presence of the chloride at a temperature below that of the operating temperature. While some improvement in overall catalyst performance has been reported using these methods, the pre-soaking and conditioning nonetheless impose a substantial delay before normal ethylene oxide production can begin after oxygen is added into the feed. This delay in production may either partially or entirely negate the benefit of increased selectivity performance of the catalyst. Additionally, in order to reduce the deleterious effects on catalyst performance caused by over-chloriding during the pre-soak phase, it is often necessary to conduct an additional chlorine removal step where the ethylene (or some other suitable hydrocarbon such as ethane) is used at elevated temperatures to remove some of the chloride from the surface of the catalyst.

A more recent example of a proposed start-up process is disclosed in U.S. Pat. No. 7,102,022 to Evans et al., which discloses contacting a Re-containing catalyst bed with a feed comprising oxygen and holding the temperature of the catalyst bed above 260° C. for a period of time of up to 150 hours. Again, while some improvement in catalyst performance may be obtained by this method, there are also inherent disadvantages to this process, notably the high temperatures required during start-up.

Thus, the treatment methods for activating a Re-containing epoxidation catalyst disclosed in the aforementioned prior publications may provide some improvement in catalyst performance, but also have a number of deficiencies as described above. Furthermore, given the improvement that an optimized activation process can impart to the selectivity of a Re-containing epoxidation catalyst, the full range of activation processes have not been fully explored. For these reasons there is a continuing need in the art for an improved activation procedure for use in olefin epoxidation.

BRIEF SUMMARY OF THE INVENTION

The present invention relates to a method for the start-up of a process for the epoxidation of ethylene comprising the following steps: initiating an epoxidation reaction by reacting a feed gas composition containing ethylene, and oxygen, in the presence of an epoxidation catalyst at a temperature of about 180° C. to about 210° C.; adding to the feed gas composition about 0.05 ppm to about 2 ppm of moderator; increasing the first temperature to a second temperature of about 240° C. to about 250° C., over a time period of about 12 hours to about 60 hours; and maintaining the second temperature for a time period of about 50 hours to about 150 hours.

DETAILED DESCRIPTION OF THE INVENTION

All parts, percentages and ratios used herein are expressed by volume unless otherwise specified. All documents cited herein are incorporated by reference. The present invention is directed to the gas phase epoxidation of olefin to form an olefin oxide by contacting a Re-containing silver-based catalyst in a reactor with a feed that contains at least oxygen, an olefin, and a chlorine-containing moderator. It has been discovered in the present invention that by using a start-up process with specific chloride concentration ranges, temperatures and treatment times, then the Re-containing silver-based catalyst will have maximum selectivity and activity performance characteristics.

As mentioned above the chlorine moderator is utilized as part of a gas phase epoxidation of an olefin to form an olefin oxide in the presence of a silver-based catalyst. The silver-based catalyst and epoxidation process will now be described in greater detail.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The support may comprise at least about 95 wt. % alpha-alumina; preferably, at least about 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.)

Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

Epoxidation Process

The epoxidation process may be carried out by continuously contacting an oxygen-containing gas with an olefin, preferably ethylene, in the presence of the previously-described catalyst. Oxygen may be supplied to the reaction in substantially pure molecular form or in a mixture such as air. By way of example, reactant feed mixtures may contain from about 0.5% to about 45% ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction are one or more chlorine moderators non-limiting examples of which include organic halides such as $C_1$ to $C_8$ halohydrocarbons; especially preferred methyl chloride, ethyl chloride, ethylene dichloride, vinyl chloride or mixtures thereof. Also suitable are hydrogen-free chlorine sources such as perhalogenated hydrocarbons and diatomic chlorine are particularly effective as moderators in gas phase epoxidation. Perhalogenated hydrocarbons refer to organic molecules in which all of the hydrogen atoms in a hydrocarbon have been substituted with halogen atoms; suitable examples are trichlorofluormethane and perchloroethylene. It is important that the concentration level of the moderator be controlled so as to balance a number of competing performance characteristics; for example, moderator concentration levels that result in improved activity may simultaneously lower selectivity. Controlling moderator concentration level is particularly important with the rhenium-containing catalysts of the present invention, because as the rhenium-containing catalysts age the moderator concentration must be carefully monitored so as to continually increase, within very small increments, because optimal selectivity values are obtained only within a narrow moderator concentration range.

A usual method for the ethylene epoxidation process comprises the vapor-phase oxidation of ethylene with molecular oxygen, in the presence of one of the aforementioned described catalysts, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the olefin oxide, un-used reactants, and byproducts to exit the reactor chamber.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The resulting ethylene oxide, which exits the reactor through the reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts including carbon dioxide.

The previously-described catalysts have been shown to be particularly selective for oxidation of ethylene with molecular oxygen to ethylene oxide especially at high ethylene and oxygen conversion rates. The conditions for carrying out such an oxidation reaction in the presence of one of the above-described catalysts broadly comprise those described in the prior art. This applies to suitable temperatures, pressures, residence times, diluent materials, moderating agents, and recycle operations, or applying successive conversions in different reactors to increase the yields of ethylene oxide. The use of one of the above-described catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

The above paragraphs described the typical operating conditions of the epoxidation process; the present invention is particularly directed to the start-up of fresh Re-containing epoxidation catalyst that precedes the normal operation of ethylene oxide production. In this start-up process, the fresh catalyst is heated to a first temperature of about 180° C. to about 210° C., which is sufficient to initiate an epoxidation reaction, while pressurizing the recycle loop to the ethylene oxide reactor with a feed gas composition containing ethylene, oxygen and a suitable ballast gas such as methane or nitrogen (nitrogen is preferred). The oxygen and ethylene are initially present in small concentrations, such as about 1% to about 4% ethylene and about 0.3% to 0.5% oxygen. The feed composition may also contain a moderator at a concentration of about 0.05 ppm to about 2 ppm, preferably about 0.5 ppm to about 1 ppm; but preferably the moderator is added immediately after reaction initiation is observed. (All concentrations recited in this paragraph are by volume).

After the epoxidation reaction is initiated as described above and as the reaction continues, the temperature is gradually increased from the first temperature to a second temperature of about 240° C. to about 250° C., preferably about 245° C. over a period of about 12 hours to about 60 hours. As the temperature is increased, the levels of ethylene and oxygen in the feed are also increased to boost the production level of ethylene oxide, as measured by ΔEO in the reactor effluent, to greater than about 0.6%, preferably greater than about 1.5%. Accordingly during this stage of the start-up process, the feed gas composition will contain about 4% to about 20% of ethylene and about 3% to about 5% oxygen. Chloride levels are maintained at the same levels as in the previous step.

After reaching the second temperature, the temperature is maintained or held for a time period of about 50 hours to about 150 hours—during which time the ethylene and oxygen concentration in the feed gas are further increased until ethylene oxide production levels comparable to full production levels are reached, during which the ΔEO is greater than about 2.0%, preferably greater than about 2.5%, more preferably in the range of 2.0%-4.0%. At this point the ethylene and oxygen levels will be near or at final operating conditions and the ethylene oxide production levels comparable to full production levels at the completion of this step, the epoxidation process will then continue to operate at these conditions.

Also during this hold time the selectivity of the catalyst increases to between 85% to 90%. If during this hold period the selectivity of the catalyst remains lower than is desired, chloride levels can be adjusted incrementally upward to maintain the gradual increase of the selectivity. The start-up process recited in the present invention allows additional chloride moderators to be added to provide small upward adjustments in selectivity without having a deleterious effect on the catalyst activity or other catalyst performance characteristics which can be caused by "overchloriding".

EXAMPLE

The invention will now be described in more detail with respect to the following non-limiting example.

Rhenium-containing 7 mm catalyst pellets were charged into a reactor with a single 1" OD tube having a 7.2 meter catalyst bed. The catalyst was heated from ambient temperature to 200° C. under N gas and upon reaching 200° C., the feed gas was set to 3% $C_2H_4$, 0.3%-0.5% $O_2$, and 1% $CO_2$ (balance continuing as nitrogen). 1 ppm of ethyl chloride moderator was additionally added. Over the next 52 hours the temperature was ramped to 245° C. and $C_2H_4$ and $O_2$ were raised in stages to increase the production of ethylene oxide in the effluent while the $CO_2$ was kept constant at 1% and the chloride at 1 ppm. After reaching 245° C., the temperature was held for 59 hours during which time $C_2H_4$ and $O_2$ were further raised until 2.2% ΔEO was attained.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

We claim:

1. A method for the start-up of a process for the epoxidation of ethylene comprising:
    initiating an epoxidation reaction by reacting a feed gas composition containing ethylene, and oxygen, in the presence of an epoxidation catalyst at a temperature of about 180° C. to about 210° C., wherein said epoxidation catalyst is a rhenium-containing silver-based catalyst;
    adding to the feed gas composition about 0.05 ppm to about 2 ppm of moderator;
    increasing the first temperature to a second temperature of about 240° C. to about 250° C., over a time period of about 12 hours to about 60 hours; and
    maintaining the second temperature for a time period of about 50 hours to about 150 hours.

2. The method according to claim 1, wherein the moderator is present in a concentration of about 0.5 ppm to about 1 ppm.

3. The method according to claim 1, wherein the moderator is an organic halide.

4. The method according to claim 1, wherein the moderator is selected from the group consisting of $C_1$ to $C_8$ halohydrocarbons.

5. The method according to claim 1, wherein the moderator is selected from the group consisting of methyl chloride, ethyl chloride, ethylene dichloride and vinyl chloride.

6. The method according to claim 1, wherein the moderator is selected from the group consisting of diatomic chlorine and perhalogenated hydrocarbons.

7. The method according to claim 1, wherein during the initiating step the feed gas composition contains about 1% to about 4% ethylene, and about 0.3% to 0.5% oxygen.

8. The method according to claim 1, wherein during the increasing step the feed gas contains about 4% to about 20% of ethylene and about 3% to about 5% oxygen.

9. The method according to claim 1, wherein the second temperature is about 245° C.

10. The method according to claim 1, wherein during the maintaining step the $\Delta$EO is greater than about 2.0%.

11. The method according to claim 1, wherein during the maintaining step the $\Delta$EO is from about 2.0% to about 4.0%.

12. The method according to claim 1, wherein during the maintaining step ethylene oxide production levels comparable to full production levels are reached.

13. The method according to claim 1, wherein the selectivity during the maintaining step is from about 85% to about 90%.

* * * * *